(12) United States Patent
Sablone

(10) Patent No.: US 11,850,130 B2
(45) Date of Patent: Dec. 26, 2023

(54) APPARATUS AND A METHOD FOR MANUFACTURING LAYERED TAPES, PARTICULARLY FOR USE IN THE MANUFACTURING OF SANITARY PRODUCTS

(71) Applicant: Fameccanica.Data S.p.A., San Giovanni Teatino (IT)

(72) Inventor: Gabriele Sablone, San Giovanni Teatino (IT)

(73) Assignee: Fameccanica.Data S.p.A., San Giovanni Teatino (IT)

( * ) Notice: Subject to any disclaimer, the term of this patent is extended or adjusted under 35 U.S.C. 154(b) by 0 days.

(21) Appl. No.: 17/960,181

(22) Filed: Oct. 5, 2022

(65) Prior Publication Data
US 2023/0109228 A1    Apr. 6, 2023

(30) Foreign Application Priority Data
Oct. 6, 2021   (EP) ..................... 21201138

(51) Int. Cl.
*A61F 13/15*    (2006.01)
*B32B 37/02*    (2006.01)

(52) U.S. Cl.
CPC .. *A61F 13/15764* (2013.01); *A61F 13/15699* (2013.01); *B32B 37/02* (2013.01); *A61F 2013/15861* (2013.01)

(58) Field of Classification Search
None
See application file for complete search history.

(56) References Cited

U.S. PATENT DOCUMENTS

| | | | |
|---|---|---|---|
| 8,998,874 B2 | 4/2015 | Marche et al. |
| 9,469,091 B2 | 10/2016 | Henke et al. |
| 2020/0253789 A1 | 8/2020 | Schwartz et al. |
| 2021/0000657 A1 | 1/2021 | Hohm et al. |

OTHER PUBLICATIONS

European Search Report dated May 3, 2022. 8 pages.

*Primary Examiner* — Barbara J Musser
(74) *Attorney, Agent, or Firm* — RMCK Law Group PLC

(57) ABSTRACT

A method and an apparatus are disclosed for manufacturing layered tapes and a layered tape arrangement including a pair of layered tapes wound together. Each of the layered tapes is individually unbalanced as far as a number of layers in a cross direction, but the resulting tape arrangement is nevertheless balanced, allowing for a balanced rolling of the layered tapes in a coil, or balanced folding of the layered tape arrangement into a ply stack.

10 Claims, 2 Drawing Sheets

APPARATUS AND A METHOD FOR MANUFACTURING LAYERED TAPES, PARTICULARLY FOR USE IN THE MANUFACTURING OF SANITARY PRODUCTS

CROSS-REFERENCE TO RELATED APPLICATION

This application claims priority to European Patent Application No. 21201138.1 filed Oct. 6, 2021. The disclosure of the above application is incorporated herein by reference in its entirety.

Field of the invention

The present invention relates to the manufacturing of layered tapes, particularly for use in the manufacturing of sanitary products.

Prior art

Layered tapes (the so-called "laminates") are widely used in the manufacturing of multiple portions or parts of sanitary products. Side panels of sanitary products such as diapers are exemplary of the use of laminates in the manufacturing of sanitary products. Side panels are stretchable laminates that comprise an elastic film in the layered structure thereof. As the elastic film is has a higher costs than other materials the laminate is made of (typically nonwoven materials), designing the side panels is done with a view to sparing the elastic film as much as possible based on the required side panel performances: this generally results in the elastic film being provided over part of the width of the laminate, which means the laminate is not thickness-balanced in the cross direction. The impact of this largely depends on the width ratio between thicker sections and thinner section of the laminate: for small side panels, for instance for baby diapers, this ratio is generally high, whereby there is very little unbalance in the tape material and the later can be easily and effectively wound in a coil after manufacturing and kept at standby for further processing.

Conversely, when side panels are designed for larger sized applications, for instance bariatric diapers, the above ratio swings towards lower values, as the width of the elastic film needed to achieve the desired performance is a much smaller fraction of the total width of the tape material. Accordingly, the resulting tape material is markedly unbalanced along the cross direction, making it very difficult to wound in a coil for storage. In other terms, the thickness gradient in the cross section of the tape material leads to non-uniform winding radii along the cross section and progressively sloping winding surfaces, which lead to a deviated winding of the tape material.

OBJECT OF THE INVENTION

The object of the invention is to overcome the above mentioned technical problems. Specifically, the object of the invention is to provide balanced winding of tape materials that are unbalanced in the cross direction.

SUMMARY OF THE INVENTION

The object of the invention is achieved by an apparatus and a method having the features of the claims that follow, which form an integral part of the technical disclosure provided herein in relation to the invention.

BRIEF DESCRIPTION OF THE FIGURES

Further features and advantages of the invention will become apparent from the following description with reference to the attached figures, provided purely by way of non-limiting example, wherein.

DETAILED DESCRIPTION

Figure 1:
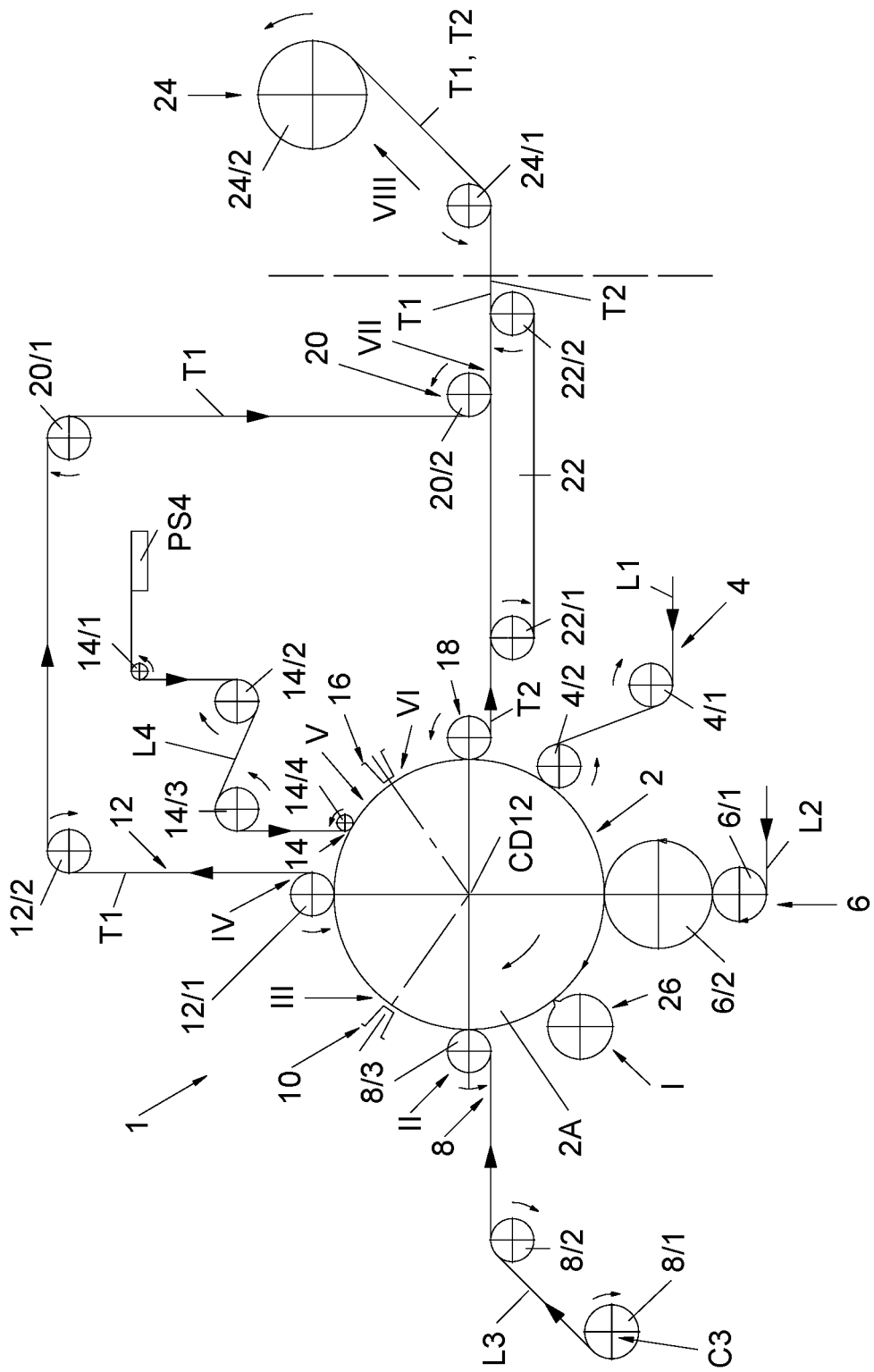
FIG. 1 is a schematic representation of an apparatus according to the invention.

Reference number 1 in FIG. 1 designates as a whole an apparatus for manufacturing layered tapes according to the invention. In various embodiments, the apparatus 1, comprises an anvil wheel 2 which operates as a functional hub that receives the output from or prepares the input for processing devices or units that are part of the apparatus 1. The anvil wheel 2 is essentially configured as a rotary drum rotatable around an axis CD12 and comprising a peripheral surface 2A which is perforated to allow air suction from the outside in, so as to hold layers laid onto the anvil wheel 2 by the above processing devices or units onto the surface 2A itself. The suction action is primarily effective in respect of gas tight or substantially gas tight layers such as stretchable films. When the layer concerned is a nonwoven material, the effect of the suction action as far as holding the layer(s) onto the surface 2A is minimal, and in any case negligible as compared to the layer tension in the machine direction MD that holds the layer concerned onto the surface 2A anyway.

As a general remark, the anvil wheel 2 allows the identification of a machine direction MD, which is a direction generally transverse to the axis CD12, and a cross direction CD, which is a direction transverse to the machine direction MD. The machine direction is generally an operating direction for the processing devices or units making up the apparatus 1, and may even be variable in orientation as the output of the processing device or unit approaches the anvil wheel 2 or the input of the processing device or unit leaves the anvil wheel 2, but still remains transverse to the axis CD12. The cross direction CD is transverse to the machine direction MD and is accordingly parallel to the axis CD12. Basically, the cross direction CD is a reference direction for some actions taken on the inputs to or the outputs from the processing units or devices while they move in the machine direction. Direction R, when referred to or displayed in the figures, denotes a radial direction incident to the surface 2A.

The apparatus 1 further comprises:
- a first layer input device 4 configured for feeding a first layer L1 to the anvil wheel in the machine direction MD, the first layer L1 comprising (FIG. 2, section I) paired first and second strips L1A, L1B extending in the machine direction MD and arranged alongside one another in the cross direction CD,
- a second layer input device 6 configured for feeding a second layer L2 (FIG. 2, section I) in the machine direction MD to the anvil wheel 2, the second layer L2 comprising paired third and fourth strips L2A, L2B extending in the machine direction MD and arranged alongside one another in the cross direction CD, the second layer input device 6 being further configured for feeding the second layer L2 onto the first layer L1 to define a first stack S1 comprising the first strip L1A and the third strip L2A, and a second stack S2 comprising the second strip L1B and the fourth strip L2B,
- a third layer input device 8 configured for feeding a third layer L3 (FIG. 2, Section II) in the machine direction MD to overlap one of the first stack S1 and the second stack S2 (stack S1 in the exemplary embodiment shown in the figures), and at least part of the other of the first stack S1 and the second stack S2. Preferably, the laying of the layer L3 is done so that it completely overlaps both stacks S1, S2 as seen in FIG. 2, section II;

a first bonding unit 10 (FIG. 2, Section III) configured for bonding the third layer L3 to said one of the first stack S1 and the second stack S2, thereby defining a first layered tape T1, a first takeaway unit 12 configured for taking the first layered tape T1 away from the anvil wheel 2, following definition thereof by the bonding unit 10, a fourth layer input device 14 (FIG. 2, Section IV) configured for feeding a fourth layer L4 in the machine direction MD to overlap the other of the first stack S1 and the second stack S2 (the latter in the exemplary embodiment shown in the figures), a second bonding unit 16 (FIG. 2, Section VI) configured for bonding the fourth layer L4 to the other of the first stack S1 and the second stack S2 (here bonding involves the stack S2), thereby defining a second layered tape T2, a second takeaway unit 18 configured for taking the second layered tape T2 away from the anvil wheel 2, and a combiner unit 20 (FIG. 2, Section VII) configured for combining the first layered tape T1 with the second layered tape T2 so that the third layer L3 of the first layered tape T1 overlaps the second stack S2 (in general said other of the first stack S1 and second stack S2), and the fourth layer of the second layered tape overlaps the first stack S1 (in general said one of the first stack S1 and second stack S2).

Preferably, the combiner unit 20 cooperates with a transfer conveyor 22 that extends the path of tape T2 enough for routing the tape T1 to combine with tape T2. The final overlap pattern between stacks Si and S2 is visible in FIG. 2, section VII. Such configuration is preferred as it is optimal for subsequent winding of the assembly of layered tapes L1, L2 into a coil 24, see FIG. 2, Section VIII.

Figure 2:
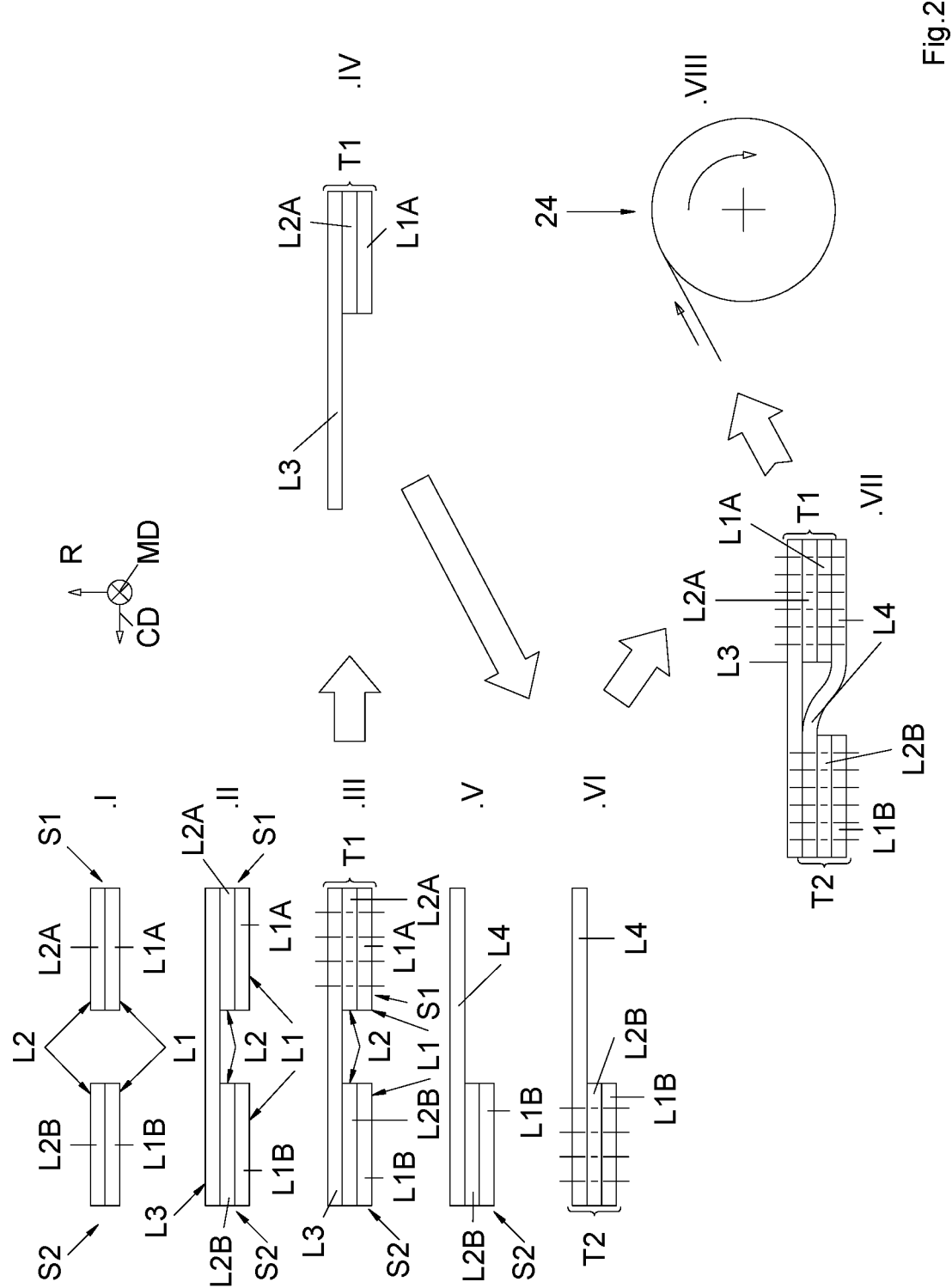
FIG. 2 is a schematic representation of method steps according to the invention, and includes sections I through VIII which are also reproduce in FIG. 1 to locate the method steps concerned relative to the apparatus of FIG. 1.

As a general remark, the meaning of which will be apparent from the disclosure that follows, the schematic views making up FIG. 2 are meant to provide a reference representation of what happens to the layers L1-L4 through the different method steps, and it is in no way to be meant as limiting or fully illustrative of actual processing conditions of the embodiments. For instance, while stacks S1 and S2 are here represented as being separated by a substantial gap therebetween, in embodiments such gap may be comparatively smaller or quasi-zero based depending on the processing conditions. Additionally, while the thickness of the layers is represented as generally uniform, the same may vary based on the materials involved and/or specific design choices. Similarly, the dimension of the layers L1-L4 in the cross direction CD (namely the width) may in reality deviate from the schematic representation above, be it on account of deliberate design choices envisaging asymmetric stacks Si and S2, or else to layer properties, for instance elastic stretchability of layer L2 (which may affect layer thickness as well).

In preferred embodiments, layers L1, L3, and L4 are made of or comprise a nonwoven material, and in general of a material that is not designed to be processed by stretching/elastic stretching thereof, for instance in the cross direction CD.

In such embodiments, the layer L2 is made of or comprises a stretchable material, for instance a stretchable film that can be stretched in the cross direction CD (and in the machine direction MD as well, although the latter may not be of interest for a number of applications).

Accordingly, the layer input devices 4, 8, 14 and the takeaway units 12, 18 are generally configured as feeding units wherein the layer of material negotiates a path through one or more rollers (drive rollers and deviation rollers) while being unwound or otherwise taken from a buffer comprising a coil or a ply stack. The same applies, i.e., to the combiner unit 20 and to the transfer conveyor 22.

Purely by way of example, and without the description or the figure implying whatsoever limitation in respect of embodiments of the invention, FIG. 2 displays an exemplary arrangement of the devices 4, 8, 12, 14, 18, 20, 22 wherein the rollers defining the path negotiated by layers L1, L3, L4 and tape T1 are identified by the same reference numbers as the device they belong to, suffixed by a progressive identifier (i.e. 1, 2, 3, etc.) separated by a slash. The representation of each roller associated to the corresponding direction of rotation. Accordingly:

the first layer input device 4 comprises a first roller 4/1, and a second roller 4/2, both configured as deflection rollers, and roller 4/2 also configured as a laydown roller configured for laying the layer L4 down onto the anvil wheel 2 (and on top of other layers possibly present thereon). The first layer L1 is drawn from, equivalently, a coil or a ply stack;

the third layer input device 8 comprises a first roller 8/1, a second roller 8/2 and a third roller 8/3. Roller 8/1 is a coil mounting shaft wherein a coil C3 of the layer L1 (e.g. a non-woven material) is fitted, roller 8/2 is a deflection roller, and roller 8/3 is a laydown roller (also bringing some deflection to the layer L3) that is configured for laying the layer L3—drawn from the coil C3—down onto the anvil wheel 2 (and on top of other layers possibly present thereon);

the takeaway unit 12 comprises a first roller 12/1 and a second roller 12/2, the former being a takeaway roller, the latter a deflection roller;

the fourth layer input device 14 comprises a first roller 14/1, a second roller 14/2, a third roller 14/3, and a fourth roller 14/4, wherein rollers 14/1 to 14/3 are deflection rollers, while roller 14/4 is a laydown roller configured laying the layer L4—drawn from a ply stack PS4—down onto the anvil wheel 2 (and on top of other layers possibly present thereon), the takeaway unit 18 comprises a single roller 18/1 (a takeaway roller), however it cooperates with the transfer conveyor 22 (rollers 22/1 and 22/2) to relay the tape T2 to a combination location with the tape T1 the combiner unit 20 also feature first and second rollers 20/1 and 20/2, the latter being a laydown roller configured for laying the tape T1 onto the newly formed tape T2. It is noted that the combiner unit 20 may be provided as a section of the takeaway unit 12, as it actually takes the tape Tl over from the latter: accordingly, the combiner unit 20 may simply be practiced as an extension of the takeaway unit 12 configured for drawing the tape T1 to the meeting location of tapes T1 and T2 (FIG. 2, section VII).

Based on the design of the layer input devices, the takeaway units, and the combiner unit above, one or more of the rollers mentioned in the foregoing may be provided with layer drive functions as well, i.e. they can be configured for drawing the respective layer L1, L2, L3, L4 from the corresponding storage facility (coil, ply stack, etc.)

As to the processing of layer L2, in the preferred embodiments wherein the layer comprises an elastically stretchable film, the layer input device 6 is configured differently from the remainder of the layer input devices 4, 8, 14. Specifically, the layer input device 6 is arranged as a stretcher device configured for stretching the layer L2 in the cross direction CD. To this end, a first roller 6/1 deflects the layer L2 and conveys the same to a stretcher roller 6/2. The stretcher roller 6/2 may be practiced as a conventional single track stretcher configured for processing a single strip of layer L2 and stretching the same in the machine direction, or as a double track stretcher as disclosed in European patent application no. 21189781.4 in the name of the same applicant. The latter is configured for simultaneously processing two parallel strips of stretchable material to provide stretching in the cross direction CD. In both cases, in a manner per se known, the stretchable material is held onto peripheral edges of stretcher discs having a variable mutual distance in the cross direction CD by means of suction devices, whereby the stretchable material is forced to accommodate the variation, particularly the increase, in the mutual distance between stretcher discs as it winds around the same, thereby undergoing stretching in the cross direction CD. When the layer L2 is eventually laid down onto the layer L1 in a stretched condition, stretching of the layer L2 in the cross direction is maintained by suction of the layer L2 (which presses the layer L1 onto the anvil wheel 2 too in the process). Suction is made effective by the increased gas tightness of the stretchable layer L2 as compared to the nonwoven material of the layer L1, whereby layer L2 maintains the stretched condition set up by the stretcher roller 6/2.

When the stretcher roller 6/2 is embodied as a single track stretcher, a cutting device 26 is conveniently provided downstream of the layer input unit 6 at the anvil wheel 2, to split the stacked layers L1, L2 in paired first and second strips L1A, L1B, L2A, L2B, and into stacks S1, S2 accordingly.

Alternatively, when the stretcher roller 6/2 is embodied as a double track stretcher as noted above, the first layer input device 4 is provided with a paired arrangement as well, whereby the layer L1 is fed already separated into paired strips L1A, L1B, and paired strips L2A, L2B are individually stretched by the roller 6/2 and individually laid onto the paired strips L1A, L1B as shown in FIGS. 2, sections I through VII. In such embodiments the cutting device 26 may not be provided for, as it the stacks S1, S2 are already virtually preformed prior to laying the layer L2 onto the layer L1. However, in some embodiments the cutting device 26 may nevertheless be provided for, especially when the layer input device 4 is not provided with a paired arrangement. In these embodiments, the strips L2A and L2B are individually laid down in a stretched condition onto the unitary layer L1, wherefrom strips L1A and L1B are then separated by the cutting device 26 operating between the strips L2A and L2B without interacting with them.

Bonding units 10 and 16 are preferably configured as ultrasonic bonding units configured to provide a welding pattern onto the to-be layered tape being assembled onto the anvil wheel 2. Bonding units 10 and 16 are typically configured to provide spot-like welding patterns that permanently bond layers L1, L2, L3 (bonding unit 10) or L1, L2, L4 (bonding unit 16) together while allowing shrinking of the layer L2 to the original, unstretched, condition thereof after bonding, and following removal of the stretch-maintaining condition—in this case the suction onto the anvil wheel 2. The latter is generally removed upon takeaway of the newly formed tapes T1, T2 off the anvil wheel 2, which defeats the suction holding the tape(s) onto the anvil wheel 2 itself. In a way per se known, shrinking of the layer L2 (each individual strip) back to the original unstretched configuration thereof provides the tapes T1, T2 with a three-dimensionally textured elastic core.

Overall, the apparatus 1 according to the invention operates according to a method for manufacturing layered tapes (or laminates) that is itself part of the invention.

In various embodiments, the method for manufacturing layered tapes T1, T2 according to the invention, comprises (clockwise sweep through FIG. 2):

feeding the first layer L1 in the machine direction MD, the first layer L1 comprising paired first and second strips L1A, L2A extending in the machine direction MD and arranged alongside one another in the cross direction CD feeding the second layer L2 in the machine direction MD, the second layer L2 comprising paired third and fourth strips L2A, L2B extending in the machine direction MD and arranged alongside one another in the cross direction CD, applying the second layer L2 onto the first layer L1, thereby defining the first stack S1 comprising the first strip L1A and the third strip L2A, and the second stack S2 comprising the second strip L1B and the fourth strip L2B, the first stack S1 and the second stack S2 are arranged alongside one another in the cross direction (FIG. 2, section I), feeding the third layer L3 in the machine direction MD, the third layer L3 extending in the machine direction MD and extending in the cross direction CD to overlap one of the first stack S1 and the second stack S2 (here the stack S1), and at least part of the other of the first stack S1 and the second stack S2 (here the stack S2)—FIG. 2, Section II, bonding the third layer L3 to said one of the first stack S1 and the second stack S2 (in view of the foregoing, boding involves the stack S1), thereby defining the first layered tape T1 (FIG. 2, Section III), and taking away the first layered tape T1 (FIG. 2, Section IV), feeding a fourth layer L4 in the machine direction MD, the fourth layer L4 extending in the machine direction MD and extending in the cross direction CD to overlap the other of the first stack S1 and the second stack S2 (here the stack S2)—FIG. 2, Section V, bonding the fourth layer L4 to the other of the first stack S1 and the second stack S2 (in view of the above, bonding involves the stack S2), thereby defining the second layered tape T2, and taking away the second layered tape T2 (FIG. 2, section VI)

combining the first layered tape T1 with the second layered tape T2 so that the third layer of the first layered tape overlaps the other of said first stack S1 and second stack S2 (here the stack S2), and the fourth layer of the second layered tape overlaps said one of the first stack S1 and the second stack S2 (here the stack S1).

Feeding the first layer L1 in the machine direction MD is carried out by the layer first layer input device 4: the layer L1, a nonwoven material in preferred embodiments, is drawn from a storage or a buffer (e.g. a coil or a ply stack) and laid down onto the anvil wheel 2. Tension applied to the layer L1 sticks the layer L1 onto the surface 2A (the suction, as noted, results in minimal adhesion force, if at all), whereby surface 2A becomes lined—as far as the extension of the layer L1—with the layer L1 itself. As noted above, the layer L1 can be fed as a single, unitary layer wherein the strips L1A, L1B are yet to be cut off one another, or already partitioned into the strips L1A, L1B.

Next, feeding the second layer L2 in the machine direction MD is effected by the second layer input device 6. In the preferred embodiments wherein the layer L2 is a stretchable material (elastically stretchable) the input device 6 provides stretching of the layer L2 in the cross direction as disclosed above prior to applying the layer L2 onto the layer L1. Stretching is maintained even after the layer L2 (whether a unitary layer or arranged in paired strips) leaves the stretcher roller 6/2: the suction at the surface A2 adheres the layer L2 to the layer L1 also taking advantage of the increased gas tightness of the layer L2 as compared to the layer L1. This results, whether the strips are already cut off one another or not, in stacking of the first strip L1A and the third strip L2A, and stacking of the second strip L1B and the third strip L2B.

Following this, if the layer L1 and/or the layer L2 are not input or laid down onto the anvil wheel 2 as paired strips, a cutting stage is envisaged wherein the cutting unit 26 splits the layer(s) in the machine direction MD, thereby defining the first stack S1 and the second stack S2 as separate stacks.

Feeding the third layer L3 in the machine direction MD is done via the third layer input device 8: the layer L3 is drawn from the coil C3 (or, equivalently, a ply stack) and laid down onto the stacks S1 and S2 by the laydown roller 8/3. The third layer L3 extends in the cross direction CD to overlap the first stack S1 and at least part of the second stack S2 (the other way around is of course possible) as shown in FIG. 2, Section II. The extent of the overlap between the stack S2 and the layer L3 is variable based on the dimension of the layer L3 in the cross direction CD, but it is preferred that in addition to a full overlap with the stack S1, the layer L3 fully overlaps the stack S2, essentially ending at the edge of the stack S2 itself.

Stretching of the layer L2 in the cross direction CD is maintained by virtue of the suction ad the surface A2 described above during laying of the layer L3, which however is adhered to the layers L2, L1 and to the anvil wheel 2A essentially by the tension thereof in the machine direction MD, as suction from the anvil wheel 2 is prevented from making it through the layer L2.

These are the conditions in which bonding of the third layer L3 to the first stack S1 is effected, thereby defining the first layered tape T1 (FIG. 2, Section III). As noted in the foregoing, bonding is preferably provided as ultrasonic bonding over a spot-like pattern. Ultrasonic bonding is achieved by cooperation between an ultrasonic horn of the bonding unit 10 and the anvil wheel 2 whereon the layers L1, L2, L3 are arranged.

Bonding only involves the stack S1, while the stack S2 is left adhered to the anvil wheel 2, but with the layers thereof still unbonded. Stretching of the layer L2 is maintained exactly for the same reasons as noted above, and it is generally maintained as long as the layer L2 or a portion thereof (e.g. a single strip out of the initial two) adheres to the anvil wheel 2 together with any intervening layer(s).

The layered tape T1 is accordingly formed, and it is ready to be taken away by the first takeaway unit 12. It is at this stage that the suction exerted at the surface 2A is defeated, thereby releasing the cross direction stretching on the layer L2 of the tape T1. The tape T1 takes the way of a buffer stretch through and across the takeaway unit 12 and the combiner unit 20, the latter preferably configured as an end portion of the takeaway unit 12, whereby the combiner unit 20 and the takeaway unit 12 may in some embodiments actually merge into a single device or unit.

Feeding the fourth layer L4 in the machine direction MD is effected in a manner altogether similar to feeding of the third layer L3, and involves the fourth layer input device 14. The latter draws the layer L4 (preferably a nonwoven material, even more preferably identical to the material of the layer L3) from the ply stack PS (or equivalently from a coil) and lays it down onto the anvil wheel 2 over the remaining stack S2. The layer L4 is, similarly to the layer L3, held onto the anvil wheel 2 by the tension thereof in the machine direction.

As with the layer L3, the layer L4 extends in the cross direction CD over the stack S2, whereby it overlaps the stack S2 and extends further in the cross direction—FIG. 2, Section V. Preferably, the dimension of the layer L4 in the cross direction CD I identical to that of the layer L3.

These are the conditions in which bonding of the fourth layer L4 to the second stack S2 is effected, thereby defining the second layered tape T2 (FIG. 2, Section VI). As with the tape T1, bonding is preferably provided as ultrasonic bonding over a spot-like pattern. Ultrasonic bonding is achieved by cooperation between an ultrasonic horn of the bonding unit 16 and the anvil wheel 2 whereon the layers L1, L2, L4 are arranged. Bonding only involves the stack S2, as the stack S1 has already been taken away with the tape T1. Stretching of the layer L2 is maintained exactly for the same reasons as noted above, and it is generally maintained as long as the layer L2 adheres to the anvil wheel 2 together with any intervening layer(s).

The layered tape T2 is accordingly formed, and it is ready to be taken away by the first takeaway unit 18, also releasing the stretching of the layer L2 of the stack S2 in the cross direction upon takeaway. The transfer conveyor makes for the buffer stretch introduced by the combination of the takeaway unit 12 and the combiner unit and relays tape T2 to a combination location at the laydown roller 20/2 of the combiner unit. Here—FIG. 2, Section VII—tapes T1 and T2 are stacked so that the third layer L3 of the tape T1 overlaps the second stack S2, and the fourth layer L4 of the second layered tape T2 overlaps the first stack S1. Note that due to the layer arrangement, absent any twisting action that flips the tape T1 over, the final stacking of the tapes T1, T2 will generally involve portions of the layer L4 (or L3) alternately on opposite sides of the stacks S1, S2 while the layer L3 (or L4) consistently on the same side of the stacks S1, S2 and in partly contact with the layer L4 (or L3). At any rate, the result is a quasi-uniform four layered stacked tape arrangement which can be easily wound on a coil 24 without any significant lack of balance in the cross direction CD (the bridging portions of layers L3 and L4, which stand alone between the stacks S1, and S2, do not affect balancing of the stacked tape arrangement). In other terms while each of the layered tape T1, T2 is individually unbalanced as far as the number of layers in a cross direction, the resulting tape arrangement is nevertheless balanced, allowing for a balanced rolling of the layered tapes into the coil 24 or, alternatively, balanced folding of the tape arrangement into a ply stack.

Tapes T1 and T2 may be used for a variety of purposes, especially in the manufacturing of sanitary products. One preferred application is the manufacturing of bariatric diapers, wherein tapes T1 and T2 can be used to manufacture the so called "ears" of the diaper, i.e. stretchable waist band portions that protrude laterally of the chassis and that are configured to connect to portions of the chassis itself to seal the diaper waist line. Tapes T1 and T2 can be unwound together from the coil 24 and cut into sections making up the ears. The cross sections of the tapes T1 and T2 are symmetrical with respect to the machine direction MD, hence they are readily usable as left and right ears precursors, respectively (e.g. T1 as the right ear precursor, T2 as the left ear precursor).

The method and the apparatus according to the invention may also be used to manufacture layered tapes such as tapes T1 and T2 without elastic or stretching properties. In such embodiments, the layer L2 is replaced by a non stretchable layer, and the second layer input device 6 is configured as the remainder of the layer input devices. Otherwise, the method steps are unchanged, and so is the apparatus 1.

Naturally, while the principle of the invention remains the same, the details of construction and the embodiments may widely vary with respect to what has been described and illustrated purely by way of example, without departing from the scope of the present invention.

The invention claimed is:

1. A method for manufacturing layered tapes comprising:
feeding a first layer in a machine direction, the first layer comprising paired first and second strips extending in the machine direction and arranged alongside one another in a cross direction transverse to the machine direction,
feeding a second layer in the machine direction, the second layer comprising paired third and fourth strips extending in the machine direction and arranged alongside one another in the cross direction,
applying the second layer onto the first layer, thereby defining a first stack comprising the first strip and the third strip, and a second stack comprising the second strip and the fourth strip, the first stack and the second stack are arranged alongside one another in the cross direction,
feeding a third layer in the machine direction, the third layer extending in the machine direction and extending in the cross direction to overlap one of the first stack and the second stack, and at least part of the other of the first stack and the second stack,
bonding the third layer to said one of the first stack and the second stack thereby defining a first layered tape, and taking away the first layered tape,
feeding a fourth layer in the machine direction, the fourth layer extending in the machine direction and extending in the cross direction to overlap the other of the first stack and the second stack,
bonding the fourth layer to the other of the first stack and the second stack, thereby defining a second layered tape, and taking away the second layered tape,
combining the first layered tape with the second layered tape so that the third layer of the first layered tape overlaps said other of the first stack and the second stack, and the fourth layer of the second layered tape overlaps said one of the first stack and the second stack.

2. The method of claim 1, further comprising one of:
winding the combined first layered tape and second layered tape into a coil and
folding the combined first layered tape and second layered tape into a ply layer.

3. The method of claim 1 wherein the second layer comprises a stretchable material, and wherein the method further comprises stretching said second layer in the cross direction prior to applying the second layer onto the first layer, and maintaining said second layer stretched in the cross direction following application of the second layer onto the first layer.

4. The method of claim 3, wherein said bonding the third layer to said one of the first stack and the second stack is carried out while maintaining said second layer stretched in the cross direction.

5. The method of claim 3, wherein said bonding the fourth layer to the other of the said first stack and the second stack is carried out while maintaining said second layer stretched in the cross direction.

6. The method of claim 1, comprising splitting said first layer and said second layer following said applying the second layer onto the first layer, thereby separating the first strip from the second strip and the third strip from the fourth strip, and defining the first stack and the second stack.

7. The method of any of claim 3, wherein said feeding the first layer in the machine direction comprises feeding paired and separated first and second strips, and wherein said feeding the second layer in the machine direction comprises feeding paired and separated third and fourth strips.

8. The method of claim 7, wherein said stretching said second layer in the cross direction prior to applying the second layer onto the first layer comprises individually stretching the third strip and the fourth strip.

9. The method of claim 8, wherein stretching of the third strip and the fourth strip of the second layer is released upon taking away the first layered tape and upon taking away the second layered tape, respectively, whereby said combining the first layered tape with the second layered tape occurs with released stretching of the third and fourth strips of the second layer.

10. The method of claim 1, wherein said first layer, said third layer and said fourth layer each comprise a nonwoven material, and wherein said third layer and said fourth layer have substantially a same dimension in the cross direction.

* * * * *

UNITED STATES PATENT AND TRADEMARK OFFICE
CERTIFICATE OF CORRECTION

Page 1 of 1

PATENT NO. : 11,850,130 B2
APPLICATION NO. : 17/960181
DATED : December 26, 2023
INVENTOR(S) : Gabriele Sablone It is certified that error appears in the above-identified patent and that said Letters Patent is hereby corrected as shown below:

On the Title Page

(71) Applicant address information should be listed as:
- Fameccanica.Data S.p.A., San Giovanni Teatino (Chieti), ITALY -

(72) Inventor address information should be listed as:
- Gabriele SABLONE, San Giovanni Teatino (Chieti), ITALY -

(73) Assignee address information should be listed as:
- Fameccanica.Data S.p.A., San Giovanni Teatino (Chieti), ITALY -

Signed and Sealed this
Fourth Day of March, 2025

Coke Morgan Stewart
*Acting Director of the United States Patent and Trademark Office*